(12) United States Patent
Martinez-Möller et al.

(10) Patent No.: US 8,237,441 B2
(45) Date of Patent: Aug. 7, 2012

(54) METHOD AND APPARATUS FOR PROCESSING COMBINED MR/EMISSION TOMOGRAPHY RECORDINGS

(75) Inventors: Axel Martinez-Möller, München (DE); Stephan Nekolla, Esting (DE)

(73) Assignee: Siemens Aktiengesellschaft, Munich (DE)

( * ) Notice: Subject to any disclaimer, the term of this patent is extended or adjusted under 35 U.S.C. 154(b) by 373 days.

(21) Appl. No.: 12/591,177

(22) Filed: Nov. 12, 2009

(65) Prior Publication Data

US 2010/0156416 A1 Jun. 24, 2010

(30) Foreign Application Priority Data

Nov. 21, 2008 (DE) .......................... 10 2008 058 488

(51) Int. Cl.
*G01R 33/465* (2006.01)
*G01R 33/483* (2006.01)

(52) U.S. Cl. ........ 324/318; 324/307; 324/309; 324/316; 250/363.01; 250/363.04; 382/131; 382/132; 600/410; 600/425

(58) Field of Classification Search .......... 324/300–322; 382/128–133; 600/407–464; 250/363.01–363.04
See application file for complete search history.

(56) References Cited

U.S. PATENT DOCUMENTS

| | | | | |
|---|---|---|---|---|
| 6,303,935 | B1 * | 10/2001 | Engdahl et al. | 250/363.03 |
| 7,457,450 | B2 * | 11/2008 | Bruder et al. | 382/130 |
| 2006/0006641 | A1 | 1/2006 | Hada et al. | |
| 2008/0135769 | A1 | 6/2008 | Rosen | |
| 2008/0170769 | A1 * | 7/2008 | Assmann | 382/128 |
| 2010/0049032 | A1 | 2/2010 | Steinke et al. | |

FOREIGN PATENT DOCUMENTS

DE 102006033383 A1 1/2008

OTHER PUBLICATIONS

Habib Zaidi et al.: "Magnetic resonance imaging-guided attenuation and scatter corrections in three-dimensional brain positron emission tomography", Med. Phys. 30 (5), May 2003, Am. Assoc. Phys. Med. p. 937-948; Others; 2003.

(Continued)

*Primary Examiner* — Melissa Koval
*Assistant Examiner* — Emily Chan
(74) *Attorney, Agent, or Firm* — Harness, Dickey & Pierce, P.L.C.

(57) ABSTRACT

A method and an apparatus are disclosed for determining the effective count rate of photons in a combined MR/emission tomography recording. In at least one embodiment, the method includes capturing MR signals with an MR apparatus in an MR/emission tomography device for producing an MR recording of an examination object with a number of tissue types, each having a specific MR parameter; associating a number of emission tomography attenuation coefficients with the number of tissue types as a function of the MR parameter by way of an association unit, so that one emission tomography attenuation coefficient corresponds in each instance to at least one of the tissue types in the examination object; capturing photons in the examination object with an emission tomography apparatus in the MR/emission tomography device for producing an emission tomography recording; and weighting the emission tomography recording with the emission tomography attenuation coefficients by way of a correction apparatus for determining the effective count rate in the number of tissue types and for producing a corrected emission tomography recording.

22 Claims, 4 Drawing Sheets

OTHER PUBLICATIONS

M. Hofmann et al.: "MR-based PET Attenuation Correction—Method and Validation", IEEE NSS-MIC 2007; Others; 2007.

MR-based PET Attenuation Correction—Method and Validation, OASIS—Online Abstract Submission and Invitation System, Coe-Truman Technologies, Inc.; Others.

Hofmann et al.: "MRI-Based Attenuation Correction for PET/MRI: A Novel Approach Combining Pattern Recognition and Atlas Registration", J. Nucl. Med. 2008, 49, p. 1875-1883; Others; 2008.

Hofmann et al.: "A Machine Learning Approach for Determining the PET Attenuation Map from Magnetic Resonance Images", IEEE Medical Imaging Conference 2006, San Diego, CA, USA (Nov. 2006); Others; 2006.

Hofmann et al.: "MR-Based PET Attenuation Correction: Method and Validation". 2007 IEEE Nuclear Science Symposium and Medical Imaging Conference (NSS-MIC 2007)/M16-6), 1-2 (Nov. 2007); Others; 2007.

T. Beyer et al.: "MR-based attenuation correction for torso-PET/MR imaging : pitfalls in mapping MR to CT data", Eur. J. Nucl. Med. Mol. Imaging (2008) 35, p. 1142-1146; Others; 2008.

E. Zhihua Xu et al.: "A Segmented Attenuation Correction for PET", J. Nucl. Med. 1991, 32, p. 161-165; Others; 1991.

H. Zaidi et al.: "Fuzzy clustering-based segmented attenuation correction in whole-body PET imaging" Institute of Physics Publishing, Phys. Med. Biol. 47 (2002), p. 1143-1160; Others; 2002.

E. Rota Kops: "MRI Based Attenuation Correction for Brain PET Images", in Buzug TM, Holz D. et al. "Advances in Medical Engineering", Berlin, 2007, p. 93-97; Others; 2007.

Martinez-Möller, M. Souvatzoglou, R. Botnar, N. Navab, S. I. Ziegler, M. Schwaiger, S. Nekolla, An approach for MR-Based attenuation correction for combined MR/PET: effects of ignoring bones Chair for Computer Aided Medical Procedurs & Augmented Reality, Lehrstuhl für Informatikanwendungen in der Medizin & Augmented Reality; Others; Journal of Nuclear Medicine, 2007, 48 (Suppl. 2), p. 156.

* cited by examiner

METHOD AND APPARATUS FOR PROCESSING COMBINED MR/EMISSION TOMOGRAPHY RECORDINGS

PRIORITY STATEMENT

The present application hereby claims priority under 35 U.S.C. §119 on German patent application number DE 10 2008 058 488.6 filed Nov. 21, 2008, the entire contents of which are hereby incorporated herein by reference.

FIELD

At least one embodiment of the invention generally relates to a method and/or apparatus for the representation by image of functional processes in the body; and in particular it relates to a method and/or apparatus for determining the effective count rate of photons in a combined magnetic resonance/emission tomography recording, to subsequently improve emission tomography recordings.

BACKGROUND

The mapping of physiological processes in the body has become an essential resource in medical imaging. Physiological processes can be made visible here with the aid of radioactive tracers, which collect in an organ. To this end radioactive preparations are frequently used, which emit positrons, which are revealed by way of their annihilation with ambient electrons. During annihilation of the positrons pairs of collinear photons with 511 keV energy each are emitted, each reaching a detector. If the detector signals coincide, the revealed photons clearly originate from the same event. Positron emission tomography (PET) recordings of a patient can be generated in this manner.

Recordings can also be made for example using emission tomography (Single Photon Emission Computed Tomography, SPECT).

When recording emission tomography spectra and in particular PET spectra the count rates of the recordings are generally not very high due to coincidence conditions, and to achieve a good statistic efforts have been made to capture all emitted photons, such as for example all 511 keV photons from the positron annihilation. This is difficult as many photons with this energy are scattered in the surrounding tissue. The problem to be resolved is that some of the photons interact in the body before they reach the detector of the emission tomography device. In order to be able to take this interaction into account attenuation factors have to be determined for every event line, in other words the line connecting two detector segments during positron annihilation. The corresponding photon scatter loss is generally referred to as attenuation of the photons, for example of the 511 keV radiation in the tissue.

Efforts have been made in the prior art to compensate for radiation attenuation computationally at a later stage. To this end an attenuation coefficient is associated with each of the individual tissue types. The attenuation coefficient is then used to calculate the actual positron generation rate for each spatial region of the recoding (voxel).

The distribution of tissue types in the body has been determined hitherto mainly by computed tomography (CT) measurements, which allow very precise location of the individual organs.

Various approaches are known in the prior art for carrying out attenuation and scatter correction of the count rate for emission tomography recordings such as PET and SPECT.

On the one hand it is possible to derive the attenuation factors from transmission recordings with external radioactive preparations. Attenuation factors can also be used, which originate from the segmentation of transmission recordings, which were obtained with external radioactive preparations. Segmentation is carried out here to suppress noise before transfer to the emission tomography recording. Attenuation factors are also deployed, which were calculated from a geometric model of the mapped object. Finally attenuation factors are used, which were obtained from transmission recordings with x-ray sources, generally PET/CT and SPECT/CT devices.

With current PET/CT recording devices the determination of attenuation values is principally based on the CT data. More specifically the attenuation factors for each individual voxel are measured first in the attenuation map and integration is then carried out by way of each event line.

It is however not possible to carry out PET and CT measurements simultaneously and therefore at the same site. It is not possible to register both measurements (make them cover one another) without further action. Generally therefore the combination of CT and PET for determining PET attenuation coefficients has significant disadvantages due to the differing recording times of CT recording and PET recording.

The evaluation of magnetic resonance (MR) data would be desirable for determining PET attenuation coefficients. The combination of magnetic resonance and PET measurements has the advantage that these two measurements can be carried out simultaneously and at the same site. With the PET/MR recording devices the MR data can be used to determine the attenuation of 511 keV photons. Like CT measurements MR measurement also provides very precise information about the spatial arrangement of tissue in the body. The attenuation coefficients are associated with tissue regions as a function of the respective tissue type. In other words water has a different attenuation of 511 keV photons from fatty tissue.

The association of attenuation coefficients with tissue regions is however generally very complex. It must be clarified how the MR data has to be processed in order to be able to create an attenuation map, which allows a satisfactory reconstruction of PET events from the PET recording and thus provides a result, which can be compared with CT-based attenuation coefficients.

Attenuation coefficients have been examined in conjunction with neurological PET recordings for example in the following publications.

H Zaidi et al. in "Magnetic resonance imaging-guided attenuation end scatter corrections in three-dimensional brain positron emission tomography", Med Phys 2003, 30, 937-948, describe MR-based attenuation factors for PET recordings of the head, with segmentation by way of fuzzy cluster technology producing a T1-weighted MR recording. The voxels were interpreted as air, skull, brain and nasal cavities and they were allocated a theoretical, tissue-dependent attenuation coefficient, which was then subjected to Gaussian smoothing. E. Rota Kops et al. in "MRI based attenuation correaction for brain PET images" in: Buzug T M, Holz D, Bongartz J, Kohl-Bareis M, Hartmann U, Weber S, Hrsg., "Advances in Medical Engineering", Berlin, 2007; 93-97, describe the segmentation of TI-weighted MR recordings in brain, bones, soft tissue and sinuses. The attenuation coefficients, which correspond to the elementary structure and density as well as the photon energy of 511 keV, were associated correspondingly. Attenuation tables with up to four components were produced.

M. Hofmann et al. in "A machine learning approach for determining the PET attenuation map from magnetic resonance images", IEEE NSS-MIC 2006; 115, describe an approach to automating the identification of differently attenuating tissue regions.

Similarly M. Hofmann at al. in "Attenuation Correction: Method and Validation", IEEE NSS-MIC 2007, describe the registration of specific MR data in relation to an MR atlas, which is in turn registered with a CT recording. The CT-derived coefficients are then deployed in association with known relationships from local image segments.

For whole body recordings using the PET method in US2008/0135769 a method is described for correcting attenuation in a PET recording. The attenuation coefficients are derived from MR data and the PET recordings are then reworked with the attenuation coefficients.

A storage medium for producing a mapping is known from US2006/006641, being used to produce a nuclear medical image, the atlas comprising a set of magnetic resonance data and a set of correction data in association with the magnetic reference data set.

T. Beyer et al. in "MR-based attenuation correction for torso-PET/MR imaging: pitfalls in mapping MR to CT data", Nucl. Med. Mol. Imaging, 2008; 35; 1142-6 propose producing a pseudo-CT recording, which is obtained from MR data by adjusting a histogram of MR and CT data.

SUMMARY

In at least one embodiment of the invention, MR data is used to ensure a more efficient yield of emission tomography events, thereby improving identification of structures in emission tomography measurements such as PET recordings.

At least one embodiment of the invention is based on the following consideration. The attenuation coefficients for (PET) photons in each voxel (volume element of the recording) are derived from MR data using simple devices/methods and combined in a so-called attenuation map. The attenuation coefficients are then divided ("segmented") into four classes, which allow an appropriate attenuation correction for emission tomography data. The local resolution of the attenuation map is thus consciously reduced.

Specifically this means that the various attenuating tissue types of relevance for a (PET) whole body recording are first identified. Five classes were identified by the inventors in order of increasing attenuation: background, lung tissue, fatty tissue, soft tissue, bone tissue. Since the automatic identification of bone tissue is technically complex and error-prone, the bone tissue was not taken into further consideration. It turned out surprisingly that for the clinical application this did not pose any significant problem when evaluating the corrected PET recordings and can therefore be viewed as tolerable.

Bone tissue can be equated with soft tissue in respect of attenuation of the (511 keV) photons. This reduces the number of classes to be taken into account to four: background, lung tissue, fatty tissue, soft tissue. This means that there is no segmentation (identification) of bone tissue in the new attenuation map, as it is difficult to extract from the MR data. Surprisingly this does not pose any problems for the medical evaluation of the image data, even though bone tissue has a different attenuation factor from the other tissue. In order to be able to carry out an attenuation correction for the captured emission tomography and PET recordings, the attenuation maps are integrated by way of each PET event line ("line of response"), giving an attenuation table, which can be used to correct the captured PET recording.

Correspondingly at least one embodiment of the inventive method for determining the effective count rate of photons in a combined MR/emission tomography recording comprises the steps:

a) capturing MR signals with an MR apparatus in an MR/emission tomography device for producing an MR recording of an examination object with a number of tissue types, each having a specific MR parameter;

b) associating a number of emission tomography attenuation coefficients with the number of tissue types as a function of the MR parameter by way of an association unit, so that one emission tomography attenuation coefficient corresponds in each instance to at least one of the tissue types in the examination object;

c) capturing photons in the examination object with an emission tomography apparatus in the MR/emission tomography device for producing an emission tomography recording and d) weighting the emission tomography recording with the emission tomography attenuation coefficients by way of a correction apparatus for determining the effective count rate in the number of tissue types and for producing a corrected emission tomography recording.

Example embodiments of the method are characterized in that as a further feature or as a combination of further features:

a common emission tomography attenuation coefficient is associated with a number of tissue types, if their MR parameters differ by less than a predetermined threshold value;

coherent regions of identical and/or similar tissue type are identified by a spatial filter with a predetermined structure length;

the structure length is less than 5 mm, so that small-volume regions and in particular blood vessels can be identified;

of the MR parameters only the four MR parameters, which correspond respectively to a class for lung, soft tissue, fatty tissue, background, are taken into account;

a structure identification is carried out, during which in particular a sequence of three successive different MR parameters is associated with a bone structure;

the MR recording is produced with a T1 sequence measurement;

the MR recording is produced with a Dixon sequence measurement;

regions with a fat component and regions with a water component are extracted from the Dixon sequence as a function of the respective MR parameter;

the MR recording is produced with a proton-weighted sequence measurement.

The corresponding inventive apparatus of at least one embodiment for determining the effective count rate of photons in a combined MR/emission tomography recording comprises:

a) an MR apparatus in an MR/emission tomography device for capturing MR signals and for producing an MR recording of an examination object with a number of tissue types, each having a specific MR parameter;

b) an association unit for associating a number of emission tomography attenuation coefficients with the number of tissue types as a function of the MR parameter, so that one emission tomography attenuation coefficient in each instance corresponds to at least one of the tissue types in the examination object;

c) an emission tomography apparatus in the MR/emission tomography device for capturing photons in the examination object and for producing an emission tomography recording and d) a correction apparatus for weighting the emission tomography recording with the emission tomography attenuation coefficients to determine the effective count rate in the number of tissue types and for producing a corrected emission tomography recording.

Example embodiments of the apparatus comprise as a further feature or as a combination of further features that:

the association unit associates a common emission tomography attenuation coefficient with a number of tissue types, if their MR parameters differ by less than a predetermined threshold value;

a spatial filter for identifying coherent regions of identical and/or similar tissue type is provided, which has a predetermined structure length;

the structure length is less than 5 mm, so that small-volume regions and in particular blood vessels can be identified;

the association unit associates four MR parameters, which correspond respectively to a class for lung, soft tissue, fatty tissue, background;

the association unit associates a bone structure with structure with a sequence of three successive different MR parameters in a predetermined interval;

the MR apparatus is a T1 sequence apparatus;

the MR apparatus is a Dixon sequence apparatus;

the Dixon sequence apparatus comprises a phase unwrap apparatus for extracting regions with a fat component and regions with a water component;

the MR apparatus is a proton sequence apparatus.

It is for example one advantage of at least one embodiment of the present invention that the determination of the attenuation coefficients for whole body emission tomography from spatially registered magnetic resonance data can be used both in combined MR/emission tomography devices and MR/positron emission tomography units (MR/PET) as well as in MR/emission tomography units (MR/SPECT). The applicability of the invention is also not problematic: it is simple to implement, as no additional hardware is needed, no patient atlas is required and no complex algorithms are deployed. Also segmentation into the four classes can be done quickly and without major computational outlay. The inventive method is also robust and reproducible, in other words the deployed algorithms are stable and not error-prone with standard patient data.

BRIEF DESCRIPTION OF THE DRAWINGS

Further features and advantages of the invention will emerge from the description which follows of example embodiments of MR/PET measurements, with reference being made to the accompanying drawing.

FIGS. 7A and B show a Dixon MR recording separated into a fat component and water component, FIGS. 7C and D show an MR-based and CT-based attenuation map for FIGS. 7A and B.

The drawings are not to scale. Identical elements or those with the same action are shown with the same reference characters.

DETAILED DESCRIPTION OF THE EXAMPLE EMBODIMENTS

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes,"

and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

Figure 1:
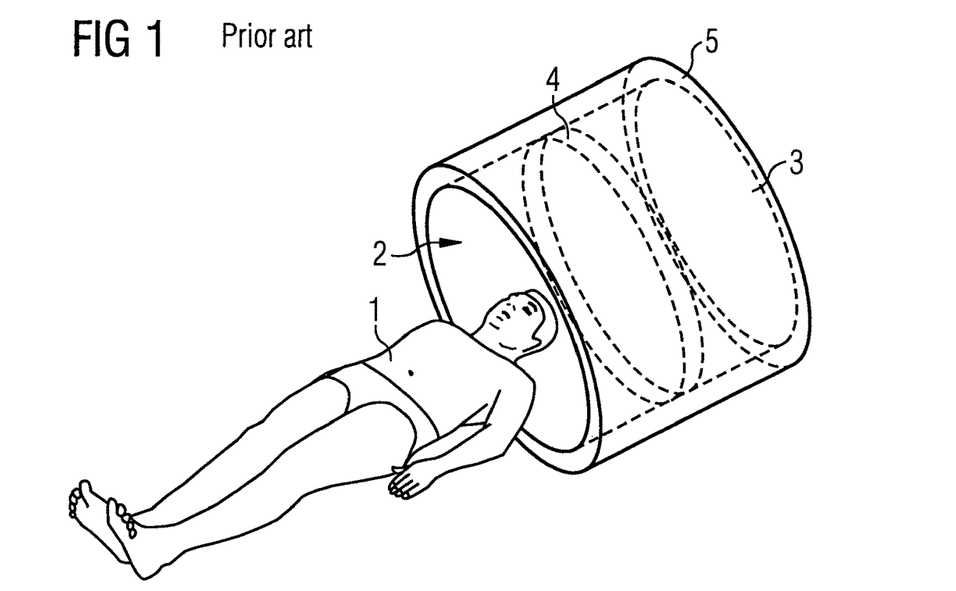
FIG. 1 shows a perspective view of a combined MRT/PET device according to the prior art.

FIG. 1 shows the combination of positron emission tomography (PET) and magnetic resonance tomography (MRT). With the combination of PET and MRT a subject 1 is brought into an examination space 2. The examination space 2 is enclosed directly by a PET apparatus 3, which comprises a detector facility 4.

In the PET apparatus 3 positrons are revealed, being released by radioactive decay in the body of the subject 1. To achieve this, corresponding drugs or preparations (radiopharmaceuticals), in which a radioactive isotope is incorporated, are administered to the subject before the examination, and become concentrated in the tissue according to the body function.

The positrons released with an initial energy between 0 eV and several MeV are scattered in the surrounding tissue and slowed down increasingly as a result. Beyond a certain kinetic energy they can be trapped by an electron and are annihilated with this after 0.1 ns to 150 ns, with generally two 511 keV photons with diametric paths being emitted.

The detector facility 4 is generally an arrangement of scintillation crystals (not shown), which are disposed in the manner of a ring around the examination space 2. In the scintillation crystals the photons with the 511 keV energy (annihilation radiation of the positrons) are converted to light quanta, which are then in turn conducted to photodetectors (not shown), preferably directly or by way of optical waveguides (not shown), which generate electrical output signals as a function of the number of light quanta.

In order to be able to associate the examination results anatomically with the PET measurement for the subject 1, the PET apparatus is combined with an MRT apparatus 5, in which an MR recording is taken at the same time as the PET recording. Both apparatuses are explained below with reference to FIG. 2, which shows a structure of a combined PET and MRT apparatus in cross section. The examination space 2 of the combined PET/MRT apparatus is defined essentially by a gradient coil 6 in a housing 7 and a high-frequency antenna facility 8. The subject 1 is partially in the examination space 2. The gradient coil 6 is disposed outside around the examination space 2, generating a magnetic field in the examination space 2. The gradient coil is only responsible for coding the spatial information. The spin is polarized or aligned by a main field magnet (not shown), which encloses the gradient coil concentrically.

Figure 2:
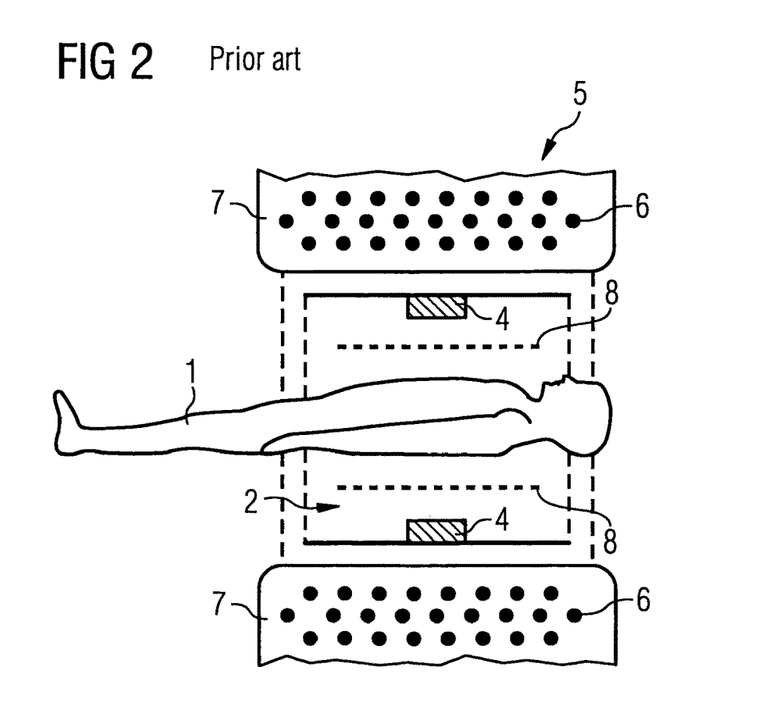
FIG. 2 shows a cross-section of the combined MRT/PET device according to FIG. 1.

The magnetic field causes the spins of the atomic nuclei in the body of the patient 1 to become aligned to some extent at least, so that the degeneration of their magnetic quantum number is suppressed. The high-frequency antenna facility 8 is used to induce transitions between no longer degenerated states. The relaxation signals of the transitions are received using the same high-frequency antenna facility and forwarded to an electronic processing unit (not shown). They are then represented graphically for the evaluation.

The MR data thus obtained can, as recognized by the inventors, be deployed particularly advantageously for correcting the attenuation and scatter of emission tomography (ET) data. In this process image processing techniques are used to associate each voxel of the MR data with one of the four classes background (air or empty space), lung, fatty tissue, soft tissue. Predetermined attenuation factors are then allocated to each of these four classes. For example the background corresponds to an attenuation factor 0/cm, lung 0.18/cm, fatty tissue 0.086/cm and soft tissue 0.1/cm. Classification is based on the MR signal intensity in the voxel (or surroundings of the voxel), so that for example not all the voxels within the lung are necessarily classed as lung. If at this site the MR signals resemble those of soft tissue, this voxel is considered as soft tissue. This can happen for example when shadows appear in the lung, which may be associated with a pulmonary edema or a region with a higher vascular density. After these steps the attenuation map contains the patient's attenuation factors for each voxel and finally the attenuation factors of other components within the examination space of the ET device (bed, electronic components) are added to the attenuation map.

Figure 3:
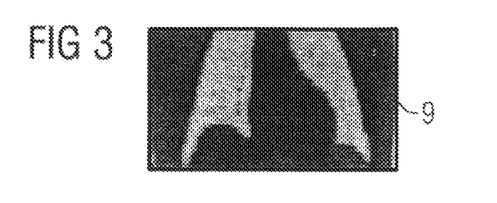
FIG. 3 shows a CT gray-scale recording of a ribcage.
Figure 4:
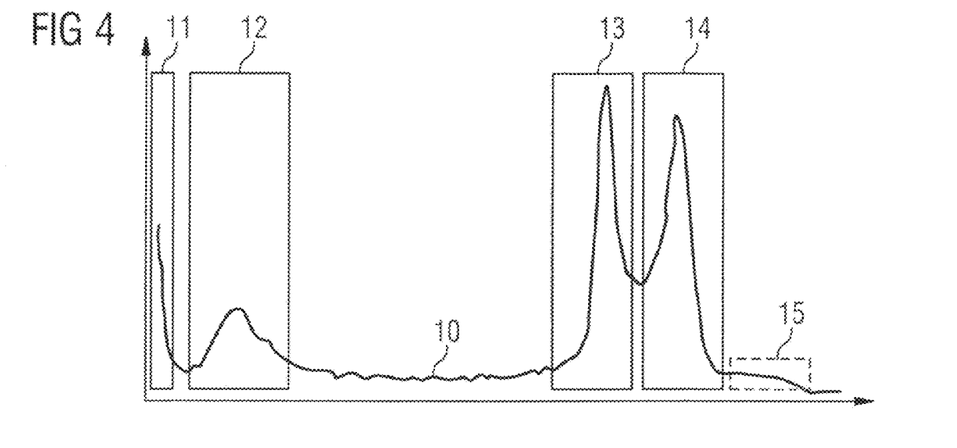
FIG. 4 shows the gray-scale histogram associated with FIG. 3.

FIG. 3 and FIG. 4 show CT recordings of the ribcage of a patient for a general understanding of the evaluation of the image data of a patient. FIG. 3 shows the CT recording as a gray-scale recording 9. This CT gray-scale recording 9 is used to produce a histogram, the curve 10 of which is shown in FIG. 4. The gray-scale values are shown on the abscissa in FIG. 4 and their frequency in the recording according to FIG. 3 is shown on the ordinate. Both scales are shown in arbitrary units. In the histogram 10 it is possible to clearly identify structures, which can be associated with individual tissue types. The recording therefore generally has a marked background signal, which depending on the representation forms an extremely light or extremely dark component in the recording. This component is shown by the frame 11 in FIG. 4.

A further tissue type in the form of lung tissue can be identified in the recording, being shown by a frame 12. Fatty tissue can also be identified in the recording and is indicated by the frame 13. Next to fatty tissue the water component in the tissue is the main component and is present as a clear signal in the region 14. Finally bone tissue contributes to the structuring of the CT gray-scale recording. As only the ribs and spinal column are taken into account in the recording layer shown in FIG. 3, the bone tissue component of the image signal is relatively minor and is shown as the most absorbing or scattering radiation in the region 15 shown with a broken line. Bone tissue generally only contributes to absorption measurements to a minor extent.

The inventors have recognized that its relatively minor contribution means that bone tissue can be ignored when deriving attenuation coefficients. This is very helpful for the usefulness of modern MR recordings for deriving attenuation coefficients.

The method for determining the effective count rate of PET events in an MR/PET recording comprises the following steps. The MR signals captured using the MR apparatus 5 of the combined MR/PET recording device are used to produce an MR recording of the examination object 1. In this MR recording, as in the CT gray-scale recording 9 according to FIG. 3, a number of tissue types can be identified, which have different gray-scale values depending on the MR parameter.

Figure 5:
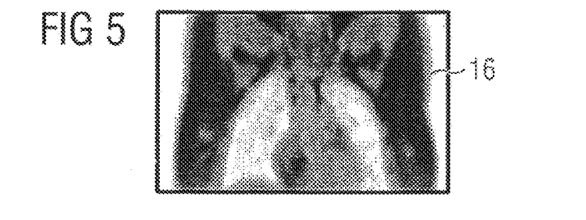
FIG. 5 shows an MR gray-scale recording of a ribcage.
Figure 6:
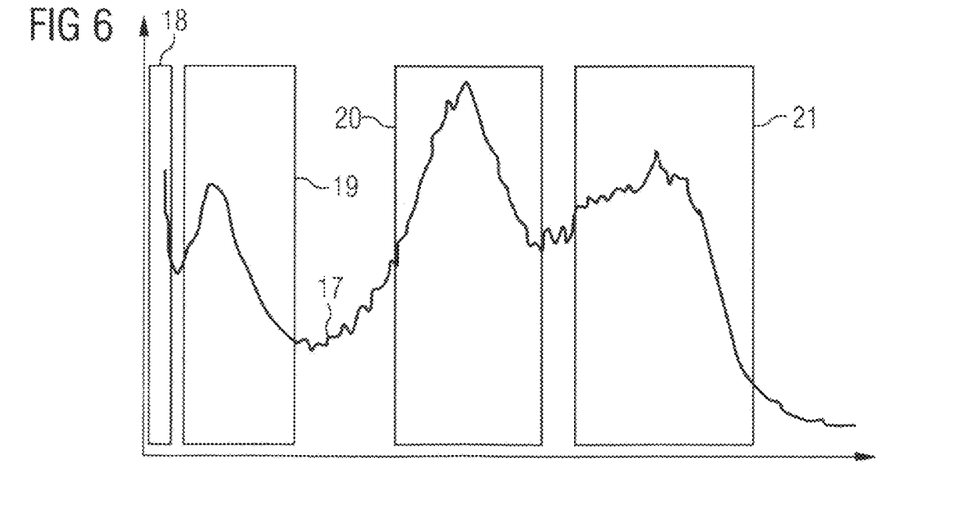
FIG. 6 shows the gray-scale histogram associated with FIG. 5.

Such an MR recording 16 is shown in FIG. 5. The gray scales in this recording correspond to different T1 values, which are in turn due to the respective chemical environment of the excited hydrogen atoms. The MR recording 16 in turn shows the image data obtained in a recording of a ribcage. A histogram 17, shown in FIG. 6, is also created for the MR recording. The background signal again represents a major component of the recording and is shown by the frame 18. The lung tissue contributes to the histogram in the region 19, while soft tissue with a large water component is responsible for the accumulation of gray-scale values in the frame 20. Finally fatty tissue is shown by gray-scale values in the frame 21. Bone tissue cannot be identified in the histogram 17 of an MR recording of the type shown by a specific gray-scale value without further action (unlike in the CT gray-scale recording 9).

The gray-scale values of the MR recording 16 in FIG. 5 correspond to the respective T1 value of the excited hydrogen atom. In addition to the T1 value, it is also possible to evaluate the phase information of the MR signal in the MR recording. This takes place in a so-called Dixon sequence recording. The inventive method can also be used with such an MR recording, as explained below with reference to FIG. 7A to 7D.

Figure 7:
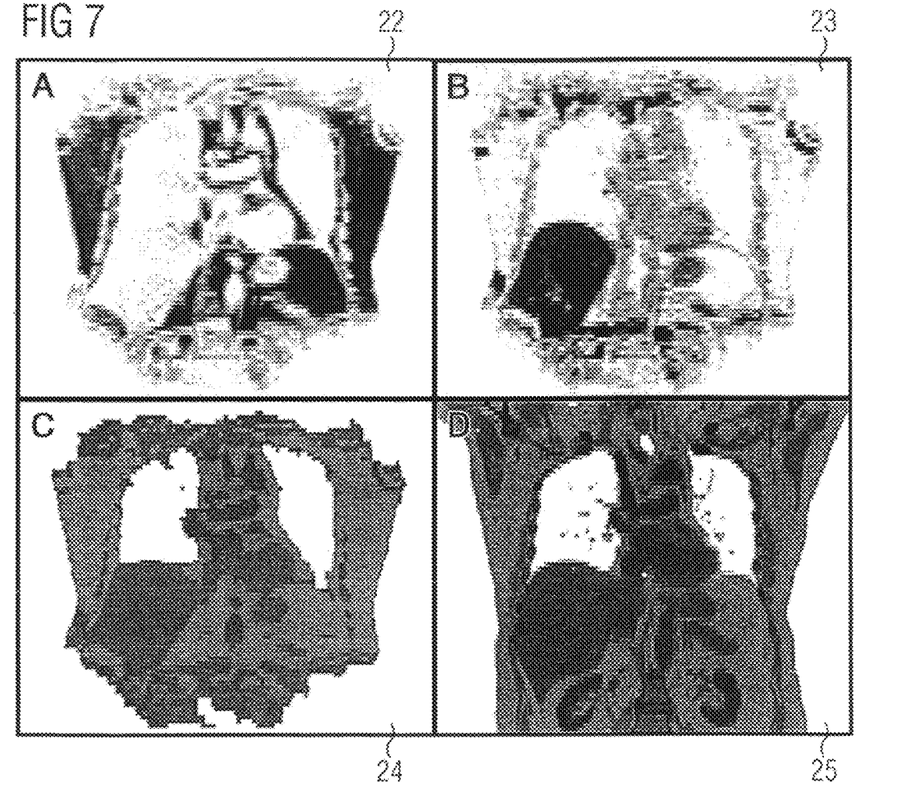

FIG. 7 compares an MR recording and a CT recording of the same examination object. FIGS. 7A and 7B show a two-point Dixon sequence recording, in which the MR signal has already been split into a fat component 22 and a water component 23. The fat component 22 in FIG. 7A and the water component 23 in FIG. 7B are essentially complementary, with both the water component and the fat component only being visible in a few organs. Each voxel in the two recordings 22 and 23 can be allocated a specific attenuation coefficient for the attenuation of PET photons. This is done in the same manner as the steps which produced an attenuation map from the T1/MR gray-scale recording 16. The attenuation coefficients derived from the fat component 22 and the water component 23 in FIGS. 7A and 7B are then combined and produce an attenuation map 24, as shown in FIG. 7C. In this attenuation map 24 an attenuation value is associated with each voxel in the MR partial recordings FIG. 7A and FIG. 7B of the fat and water components 22 and 23, which is then in turn shown in the combined attenuation map according to FIG. 7C as a gray-scale value. Preferably each voxel in the MR recording is seen here as a weighted mixture of more than one attenuation class (e.g. 30% fatty tissue 70% soft tissue), when it occurs in both diagrams 22 and 23. In this instance the voxel is allocated a correspondingly averaged value from the predetermined attenuation factors.

The attenuation map according to FIG. 7C is compared with an attenuation map 25 based on CT image data. In both maps 24 and 25 the lung tissue and larger organs with a homogeneous tissue structure can be clearly identified. Also in the two attenuation maps 24 and 25 identical attenuation coefficients can be associated with identical voxels, i.e. the gray-scale values in both maps correspond. Thus the attenuation map 24, which is based on MR data, can be used in the same manner as the attenuation map 25, which is based on CT values.

Due to its extreme gray scale, which greatly resembles the background, lung tissue is critical to evaluation of the raw MR data. In order to take into account density fluctuations in the lung tissue of one or more patients, the voxels associated with lung tissue in the MR recording are preferably allocated a variable attenuation factor, which is a function of MR signal intensity at this site.

Figure 8:
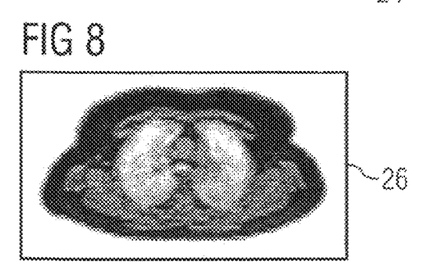
FIGS. 8 to 11 respectively show an MR recording, a CT recording, an MR-based attenuation and a CT-based attenuation.
Figure 9:
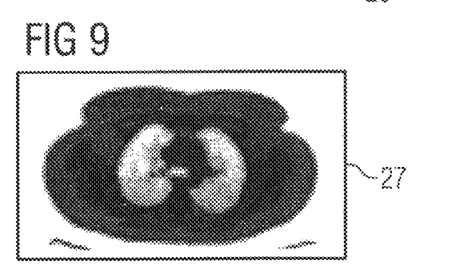

A further comparison of MR recording and CT recording with attenuation map derived therefrom is shown in FIG. 8 to FIG. 11. FIG. 8 shows an MR recording 26 of a ribcage in a horizontal plane (transaxial). A corresponding CT recording 27 is shown in FIG. 9. In both instances the position of the internal organs can be identified with similar accuracy, with bone tissue primarily visible in the CT recording.

Figure 10:
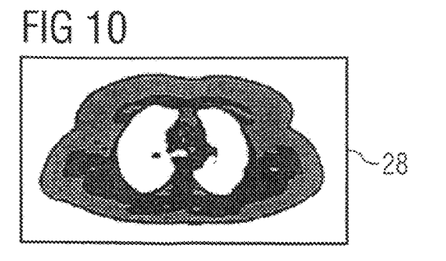
Figure 11:
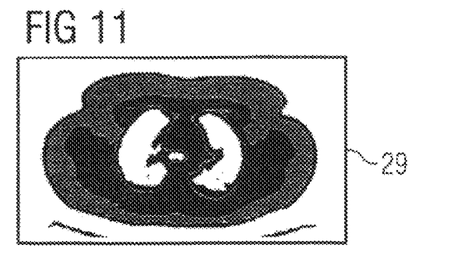

FIG. 10 shows an attenuation map 28 derived from the MR recording 26. Similarly FIG. 11 shows an attenuation map 29 derived from the CT recording 27. Distribution of the attenuation coefficients is essentially identical in both attenuation maps 28 and 29. In other words the attenuation of the PET photons in tissue can be derived both from CT recordings and from MR recordings. This means that the CT recording can be replaced by an MR recording. The MR recording has the advantage compared with the CT recording that it can be taken at the same time as the PET recording and can therefore easily be registered with the PET recording, while any displacements and movements of the patient between recordings must be taken into account when registering a CT recording and a PET recording.

The attenuation values associated with the tissue types as a function of the respective MR parameter are then applied to a raw PET recording. The processing of the PET recording with the attenuation coefficients is explained below with reference to FIG. 12 to FIG. 1.

Figure 12:
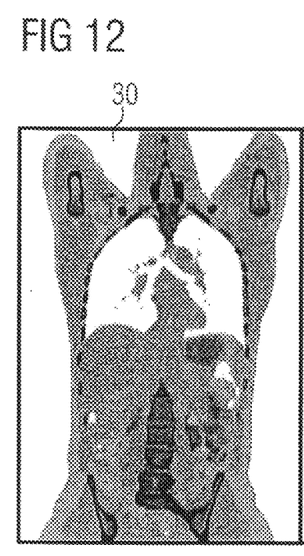
FIGS. 12 to 14 respectively show a CT-based attenuation map, a PET recording and a corrected PET recording with overlaid CT recording.
Figure 13:
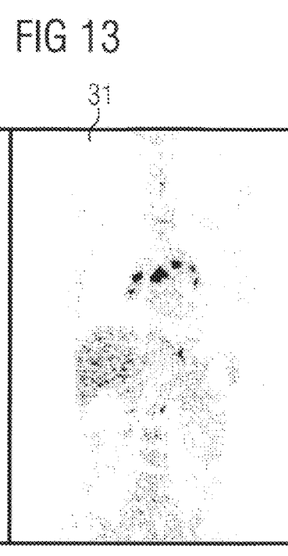
Figure 14:
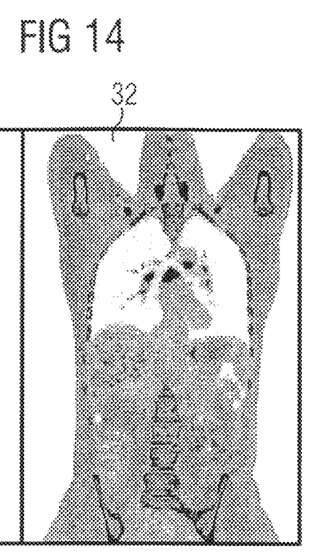

FIG. 12 shows a CT-based attenuation map 30 of a whole body recording. FIG. 13 shows a PET whole body recording 31, in which denser black shows greater radioactivity. In the PET recording 31 account is already taken of the fact that only some of the radioactive radiation is revealed in the actual measurement. The PET recording 31 therefore shows the measurement results related to the attenuation map 30 as a corrected PET recording. The combined CT/PET mapping 32 is shown in FIG. 14.

Figure 15:
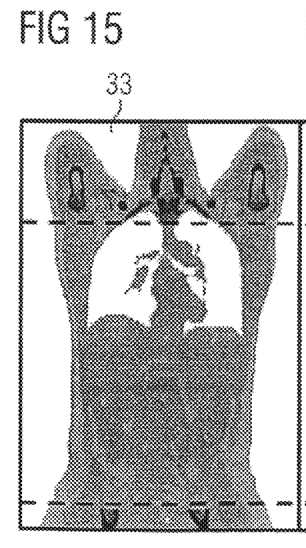
FIGS. 15 to 17 respectively show an MR-based attenuation map, a PET recording and a corrected PET recording with overlaid MR recording.
Figure 16:
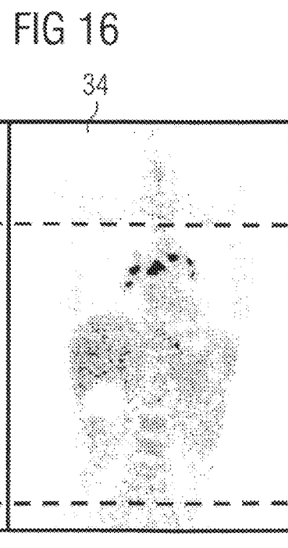
Figure 17:
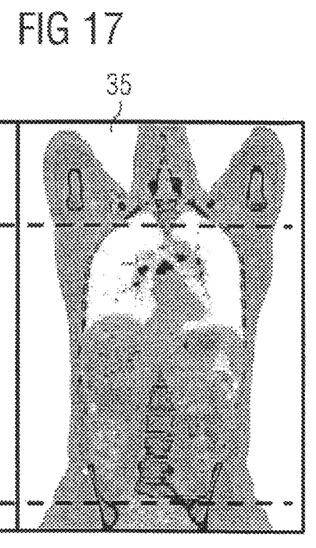

By way of a comparison with FIGS. 12 to 14, FIG. 15 to FIG. 17 show the method with MR-based attenuation coefficients. FIG. 15 shows an MR-based attenuation map 33 of a whole body recording. FIG. 16 shows a PET whole body recording 34, in which denser black indicates greater radioactivity. Account is already taken in the PET recording 34 of the fact that only some of the radioactive radiation is revealed, as some is lost in the tissue, i.e. is deflected from its original direction and thus no longer reaches the detector and can no longer trigger a coincidence signal. The PET recording 34 therefore shows the measurement results of the PET recording weighted with the MR attenuation map 33 as a corrected PET recording. The combined MR/PET mapping 35 from the MR recording and the PET recording is shown in FIG. 17 and illustrates the effective count rate of the 511 keV photons in the different tissue types.

It is evident to the person skilled in the art that to evaluate PET recordings with a local resolution that is in any case restricted, it is also possible to reduce the resolution of the MR-based attenuation maps to an optimal value, to keep the computation outlay as low as possible. To this end a common PET attenuation coefficient is associated with a number of tissue types, if their gray-scale values in the histogram (MR parameter) differ by less than a predetermined threshold value.

Also locally limited particularities should not interfere with the evaluation of the PET recordings or produce artifacts. To this end coherent regions with identical or similar tissue types are identified by a spatial filter (connected component analysis). In this spatial filter regions of identical tissue type are checked to determine whether they are directly adjacent. If so, they are identified as coherent and therefore part of a larger organ, such as the lung for example. To this end a structure length of the spatial filter is predetermined, up to which an MR parameter can be considered to be associated with an organ.

The spatial filter has proven particularly successful for lung tissue. Lung segmentation was relatively complex, as in some instances the same intensity as for the background was identified. However it was possible to differentiate here using the spatial filter, with which coherent regions and even larger regions containing air were identified.

Conversely small-volume regions and in particular blood vessels can likewise be identified and virtually replaced with adjacent tissue (morphological closing filter). This avoids any misinterpretation of voxels in the bone tissue region, heart region and aorta as air during classification into the above-mentioned four tissue classes, in particular if they show a very weak MR signal.

Generally then of the MR parameters only the four MR parameters corresponding respectively to a class for lung, soft tissue, fatty tissue, background are preferably taken into account. Irrespective of this in further preferred embodiments of the method pattern recognition algorithms can also be used. A structure identification can thus be performed, in which a sequence of three successive different MR parameters, i.e. light/dark/light, is associated with a bone structure. A further class can then be introduced, which represents bone structures and has its own predetermined attenuation factors.

At least one embodiment of the inventive method can generally be optimized for different types. Data from a number of MR recordings (captured directly or alternately one after the other) can thus be used for segmentation. This is possible for example with Dixon multipoint data or combinations of T1 and T2 data.

At least one embodiment of the inventive method was tested by experimentation with T1-weighted sequences, one-point Dixon sequences and two-point Dixon sequences, with the Dixon sequences respectively supplying a recording for the water component and the fat component. Satisfactory results were obtained in all three instances. The intensity of the recording was graded in each instance and the voxel was associated with a class as a function of its grade. In the case of the Dixon sequence where a water and fat component were simultaneously present, the voxel was considered as a mixture of both, e.g. 70% water component, 30% fat component. Otherwise the voxel was only associated with a single class. Bone margin generally showed a very low signal, which was consequently interpreted by the algorithm as background; the same happened with some voxels at the heart or in larger blood vessels due to the blood flow there. This incorrect association could be avoided with the morphological filter with a structure size of 5 mm. All structures with an extension shorter than this length were replaced with adjacent tissue. The result of the morphological filter was uniformly satisfactory.

The segmentation model can be simplified further. Instead of four classes it only has to have two or three classes (e.g. only air and soft tissue) or a mixture thereof. With such simplified segmentation it is possible to use an MR sequence which is not designed specifically for attenuation correction, so that the workflow is optimized, at the expense of a somewhat less precise attenuation correction.

For the image processing steps for segmenting the MR data it is possible to use methods of differing complexity depending on the MR sequence used. A simple threshold value approach (in combination with morphological processes to fill in voxels containing a bone margin or blood vessels) supplies good results for the segmentation of a proton-weighted sequence.

An apparatus (not shown) for carrying out the method described above, i.e. for determining the effective count rate of PET events in an MR/PET recording therefore comprises the following elements:

An MR apparatus 5 in a combined MR/PET recording device serves to capture MR signals and to produce an MR recording 16 or 26 of an examination object 1. This examination object 1 has a number of tissue types, which can be identified based on the recording spectrum with parameter values 12 to 15 or 19 to 21.

An association unit associates a number of PET attenuation coefficients with the number of tissue types as a function of the respective MR parameter, so that one PET attenuation coefficient corresponds in each instance to at least one of the tissue types in the examination object.

A PET apparatus 4 in the combined MR/PET recording device captures PET events in the examination object 1 and produces a PET recording 31 or 34.

Finally a correction apparatus weights the original PET recording with the determined PET attenuation coefficients to determine the effective count rate in the number of tissue types and to produce a corrected PET recording 35.

In this process the association unit can request a predetermined threshold value and, if the difference between MR parameters of adjacent regions is below this, a common PET attenuation coefficient is associated with a number of tissue types. This request can be made iteratively for its part where there is an iterative reduction of the local resolution.

To improve structure identification, a spatial filter in particular is provided, to identify coherent regions of identical and/or similar tissue type (connected component analysis). Something having a predetermined structure length is identified here as a coherent structure. It is possible in particular in this manner also to suppress small-volume regions, such as blood vessels in particular, if their structure length is less than 5 mm (morphological closing filter).

More generally structures can be identified based on the sequence of regions with identical MR parameters. Thus a sequence of three different MR parameters succeeding one another within a predetermined interval, corresponding perhaps to water component, fat component, water component, can be associated with a bone structure.

If the MR recording is not taken with a T1 sequence apparatus but with a Dixon sequence apparatus, i.e. with prior evaluation of the water and fat signal, this Dixon sequence apparatus can comprise a phase unwrap apparatus.

It is clear to the person skilled in the art that the embodiments of the invention are not just restricted to gray-scale mappings but that similar considerations can also be applied to representations of the MR values with graduated color tone, graduated brightness and graduated saturation.

In tests carried out patient data obtained with PET/CT and PET/MR was compared and subjected to attenuation correction. It turned out that the differences between PET/CT data and PET/MR data were minor and insignificant for the clinical application. However PET/CT registration required a greater outlay, as the PET recording could not always be taken simultaneously with the CT recording. This does not apply in the case of the combined PET/MR recording, which is a significant advantage of future systems.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combineable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, computer readable medium and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable medium and is adapted to perform any one of the aforementioned methods when run on a computer device (a device including a processor). Thus, the storage medium or computer readable medium, is adapted to store information and is adapted to interact with a data processing facility or computer device to execute the program of any of the above mentioned embodiments and/or to perform the method of any of the above mentioned embodiments.

The computer readable medium or storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

LIST OF REFERENCE CHARACTERS

1 Subject
2 Examination space
3 Positron emission tomography apparatus
4 Radiation detector for detecting positron annihilation radiation
5 Magnetic resonance tomography apparatus
6 Gradient coil
7 Coil housing
8 High-frequency antenna facility for transmitting excitation pulses and receiving magnetic resonance signals
9 CT gray-scale recording of ribcage
10 Histogram of CT gray-scale recording
11 CT background signal
12 Lung
13 Fatty tissue
14 Soft tissue
15 Bone tissue
16 T1/MR gray-scale recording of ribcage
17 Histogram of MR gray-scale recording
18 MR background signal
19 Lung
20 Soft tissue
21 Fatty tissue
22 Fat component
23 Water component
24 MR-based attenuation map
25 CT-based attenuation map
26 MR recording
27 CT recording
28 MR-based attenuation map
29 CT-based attenuation map
30 CT-based attenuation map
31 PET recording
32 CT/PET recording
33 MR-based attenuation map
34 PET recording
35 MR/PET recording

What is claimed is:

1. A method for determining the effective count rate of photons in a combined MR/emission tomography recording, the method comprising:

capturing MR signals with an MR apparatus in an MR/emission tomography device to produce an MR recording of an examination object with a plurality of tissue types, each of the plurality of tissue types having a specific MR parameter;

associating a plurality of emission tomography attenuation coefficients with the plurality of tissue types as a function of the MR parameter by way of an association unit, so that each emission tomography attenuation coefficient respectively corresponds to at least one of the plurality of tissue types in the examination object;

capturing photons in the examination object with an emission tomography apparatus in the MR/emission tomography device to produce an emission tomography recording; and weighting the emission tomography recording with the emission tomography attenuation coefficients by way of a correction apparatus for determining the effective count rate in the plurality of tissue types and to produce a corrected emission tomography recording.

2. The method as claimed in claim 1, wherein a common emission tomography attenuation coefficient is associated with a plurality of tissue types, if their MR parameters differ by less than a threshold value.

3. The method as claimed in claim 2, wherein coherent regions of at least one of identical and similar tissue type are identified by a spatial filter with a structure length.

4. The method as claimed in claim 3, wherein the structure length is less than 5 mm, so that small-volume regions are identifiable.

5. The method as claimed in claim 4, wherein the structure length is less than 5 mm so that blood vessels are identifiable.

6. The method as claimed in claim 1, wherein of the MR parameters only the four MR parameters, which correspond respectively to a class for lung, soft tissue, fatty tissue, and background, are taken into account.

7. The method as claimed in claim 1, wherein a structure identification is carried out, during which in particular a sequence of three successive different MR parameters is associated with a bone structure.

8. The method as claimed in claim 1, wherein the MR recording was produced with a T1 sequence measurement.

9. The method as claimed in claim 1, wherein the MR recording was produced with a Dixon sequence measurement.

10. The method as claimed in claim 9, wherein regions with a fat component and regions with a water component are extracted from the Dixon sequence as a function of the respective MR parameter.

11. The method as claimed in claim 1, wherein the MR recording was produced with a proton sequence measurement.

12. An apparatus for determining the effective count rate of PET events in a combined MR/emission tomography recording, the apparatus comprising:

an MR apparatus in an MR/emission tomography device to capture MR signals and to produce an MR recording of an examination object with a plurality of tissue types, each of the plurality of tissue types having a specific MR parameter;

an association unit to associate a plurality of emission tomography attenuation coefficients with the plurality of tissue types as a function of the MR parameter, so that each emission tomography attenuation coefficient respectively corresponds to at least one of the plurality of tissue types in the examination object;

an emission tomography apparatus in the MR/emission tomography device to capture photons in the examination object and to produce an emission tomography recording; and a correction apparatus to weight the emission tomography recording with the emission tomography attenuation coefficients to determine the effective count rate in the plurality of tissue types and to produce a corrected emission tomography recording.

13. The apparatus as claimed in claim 12, wherein the association unit associates a common emission tomography attenuation coefficient with a plurality of tissue types, if their MR parameters differ by less than a predetermined threshold value.

14. The apparatus as claimed in claim 13, further comprising:

a spatial filter to identify coherent regions of at least one of identical and similar tissue type, including a structure length.

15. The apparatus as claimed in claim 14, wherein the structure length is less than 5 mm so that small-volume regions are identifiable.

16. The apparatus as claimed in claim 12, wherein the association unit associates four MR parameters, which correspond respectively to a class for lung, soft tissue, fatty tissue, and background.

17. The apparatus as claimed in claim 15, wherein the association unit associates a bone structure with a sequence of three successive different MR parameters in an interval.

18. The apparatus as claimed in claim 12, wherein the MR apparatus is a T1 sequence apparatus.

19. The apparatus as claimed in claim 12, wherein the MR apparatus is a Dixon sequence apparatus.

20. The apparatus as claimed in claim 19, wherein the Dixon sequence apparatus comprises a phase unwrap apparatus to extract regions with fatty tissue and regions with soft tissue.

21. The apparatus as claimed in claim 12, wherein the MR apparatus is a proton sequence apparatus.

22. The apparatus as claimed in claim 15, wherein the structure length is less than 5 mm so that blood vessels are identifiable.

* * * * *